(12) United States Patent
Siccardi et al.

(10) Patent No.: US 11,571,199 B2
(45) Date of Patent: Feb. 7, 2023

(54) DEVICE FOR THE RETRACTION OF SOFT TISSUE IN A PATIENT UNDERGOING ARTHROSCOPIC SURGERY

(71) Applicant: MEDACTA INTERNATIONAL SA, Castel san Pietro (CH)

(72) Inventors: Francesco Siccardi, Castel san Pietro (CH); Sascha Berberich, Castel san Pietro (CH); Gianluca Parisi, Castel san Pietro (CH); Riccardo Lucchini, Castel san Pietro (CH); Matteo Ponzoni, Castel san Pietro (CH); Ernst Kehrli, Castel san Pietro (CH)

(73) Assignee: Medacta International SA, Castel San Pietro (CH)

( * ) Notice: Subject to any disclaimer, the term of this patent is extended or adjusted under 35 U.S.C. 154(b) by 442 days.

(21) Appl. No.: 16/617,737

(22) PCT Filed: May 24, 2018

(86) PCT No.: PCT/IB2018/053684
§ 371 (c)(1),
(2) Date: Nov. 27, 2019

(87) PCT Pub. No.: WO2018/220483
PCT Pub. Date: Dec. 6, 2018

(65) Prior Publication Data
US 2020/0107825 A1     Apr. 9, 2020

(30) Foreign Application Priority Data
Jun. 1, 2017   (IT) .......................... 102017000060398

(51) Int. Cl.
*A61B 17/02* (2006.01)
*A61B 17/00* (2006.01)
(Continued)

(52) U.S. Cl.
CPC ...... *A61B 17/0218* (2013.01); *A61B 17/0281* (2013.01); *A61B 2017/00323* (2013.01);
(Continued)

(58) Field of Classification Search
None
See application file for complete search history.

(56) References Cited

U.S. PATENT DOCUMENTS 5,163,949 A    11/1992   Bonutti
5,309,896 A     5/1994   Moll et al.
(Continued)

FOREIGN PATENT DOCUMENTS

JP    2009515650 A    4/2009
WO    2006110733 A2   10/2006
(Continued)

OTHER PUBLICATIONS

Australian Examination Report issued in AU 2018277165, dated Mar. 5, 2020, 4 pages.
(Continued)

*Primary Examiner* — Tessa M Matthews
(74) *Attorney, Agent, or Firm* — Meunier Carlin & Curfman LLC

(57) ABSTRACT

A device for the retraction of soft tissue in a patient undergoing arthroscopic surgery, comprising a pulling element extending in its own main direction between a first end and a second end, the latter being fitted with a hooking body configured to pass through the soft tissue of a patient and engage in the soft tissue following the traction of the pulling element towards the first end. The device further comprises a presser body suitable to press on the skin of the patient and connectable to the pulling element in at least one operating position placed at a fixed distance from the second end, wherein the fixed distance is such as to define a housing for
(Continued)

the layers of soft tissue of the patient engaged by the hooking body.

12 Claims, 6 Drawing Sheets

(51) Int. Cl.
  *A61B 90/00* (2016.01)
  *A61B 17/28* (2006.01)
  *A61B 17/29* (2006.01)
(52) U.S. Cl.
  CPC ............... *A61B 2017/00407* (2013.01); *A61B 2017/2808* (2013.01); *A61B 2017/2944* (2013.01); *A61B 2090/034* (2016.02)

(56) References Cited

U.S. PATENT DOCUMENTS

| | | | |
|---|---|---|---|
| D481,371 S | 10/2003 | Chen | |
| D556,179 S | 11/2007 | Chang | |
| D659,325 S | 5/2012 | Davis | |
| D659,329 S | 5/2012 | Davis | |
| D685,755 S | 7/2013 | Shin et al. | |
| D700,964 S | 3/2014 | Krishnan et al. | |
| D700,965 S | 3/2014 | Krishnan et al. | |
| D830,549 S | 10/2018 | Wartinbee | |
| D864,171 S | 10/2019 | Shultz et al. | |
| 11,259,929 B2 * | 3/2022 | Chin | A61B 17/00234 |
| 2005/0065409 A1 | 3/2005 | de la Torre et al. | |
| 2005/0251159 A1 | 11/2005 | Ewers | |
| 2011/0208007 A1 * | 8/2011 | Shohat | A61B 1/00087 600/227 |
| 2017/0245888 A1 * | 8/2017 | Buyda | A61B 17/3423 |
| 2018/0103942 A1 | 4/2018 | Igarashi et al. | |
| 2020/0107825 A1 | 4/2020 | Siccardi et al. | |
| 2021/0068805 A1 * | 3/2021 | Ji | A61B 10/04 |

FOREIGN PATENT DOCUMENTS

| | | |
|---|---|---|
| WO | 2007059068 A1 | 5/2007 |
| WO | 2010011674 A1 | 1/2010 |
| WO | 2011039732 A1 | 4/2011 |

OTHER PUBLICATIONS

International Search Report and Written Opinion issued by the International Searching Authority (ISA/EP) in PCT/IB2018/053684 dated Sep. 13, 2018. 14 pages.

Notice of Reasons for Refusal, in connection with JP Application No. 2019-566578, dated Nov. 16, 2020.

Notice of Failure to Disclose Information on Prior Art Documents, in connection to JP Application No. 2019-566578, dated Nov. 16, 2020.

* cited by examiner

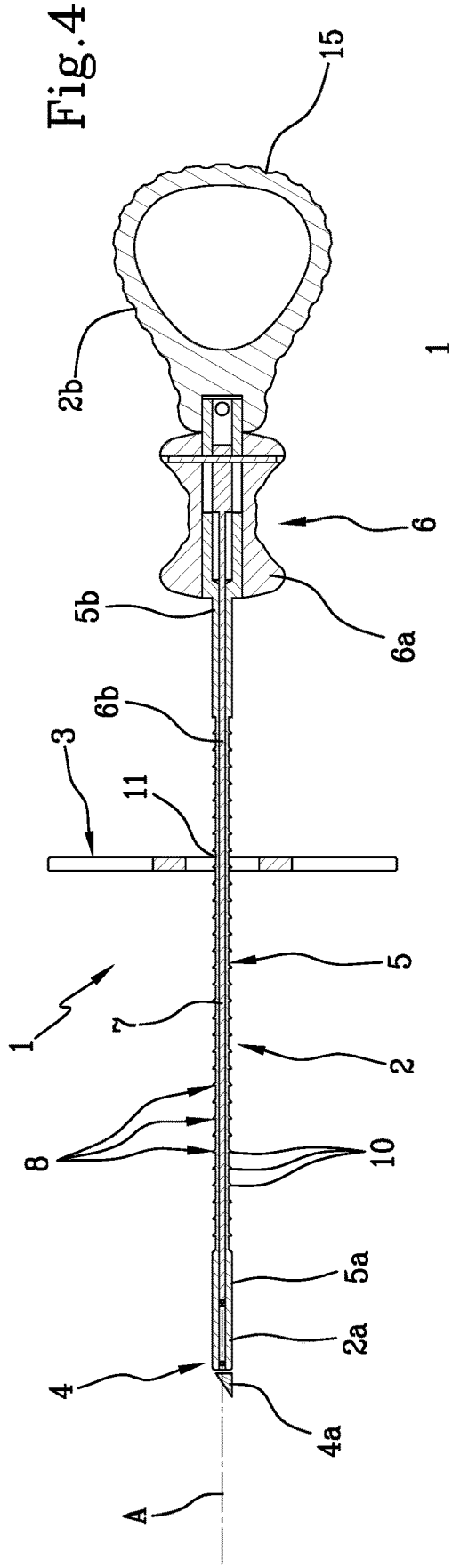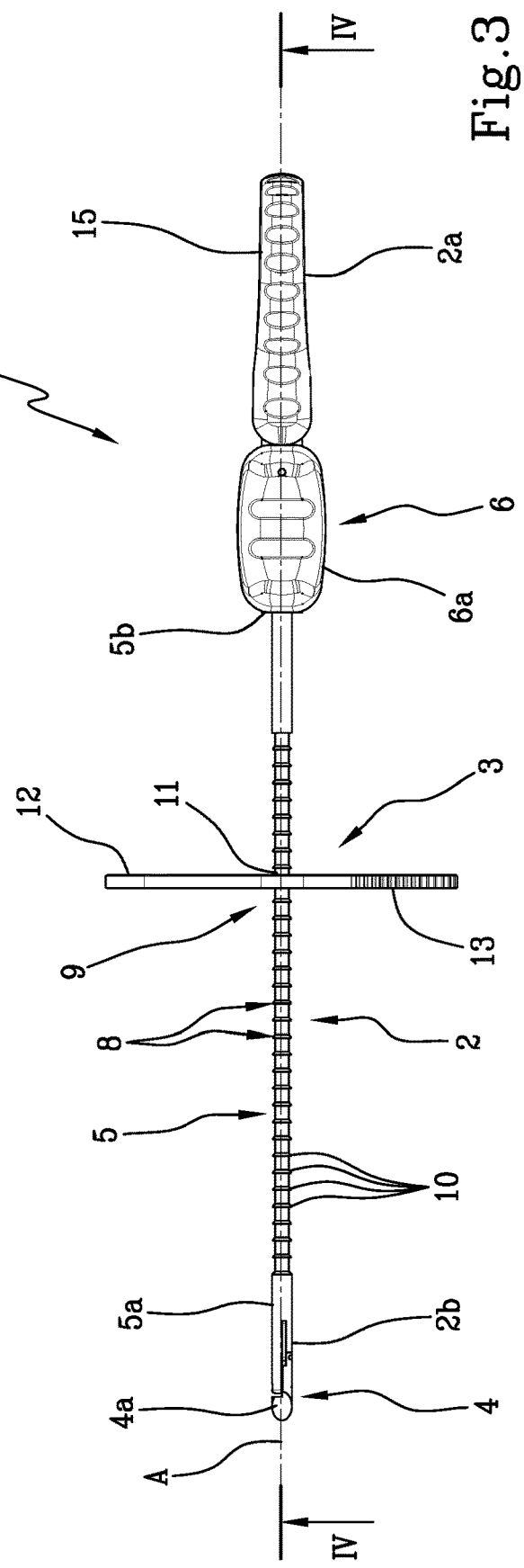

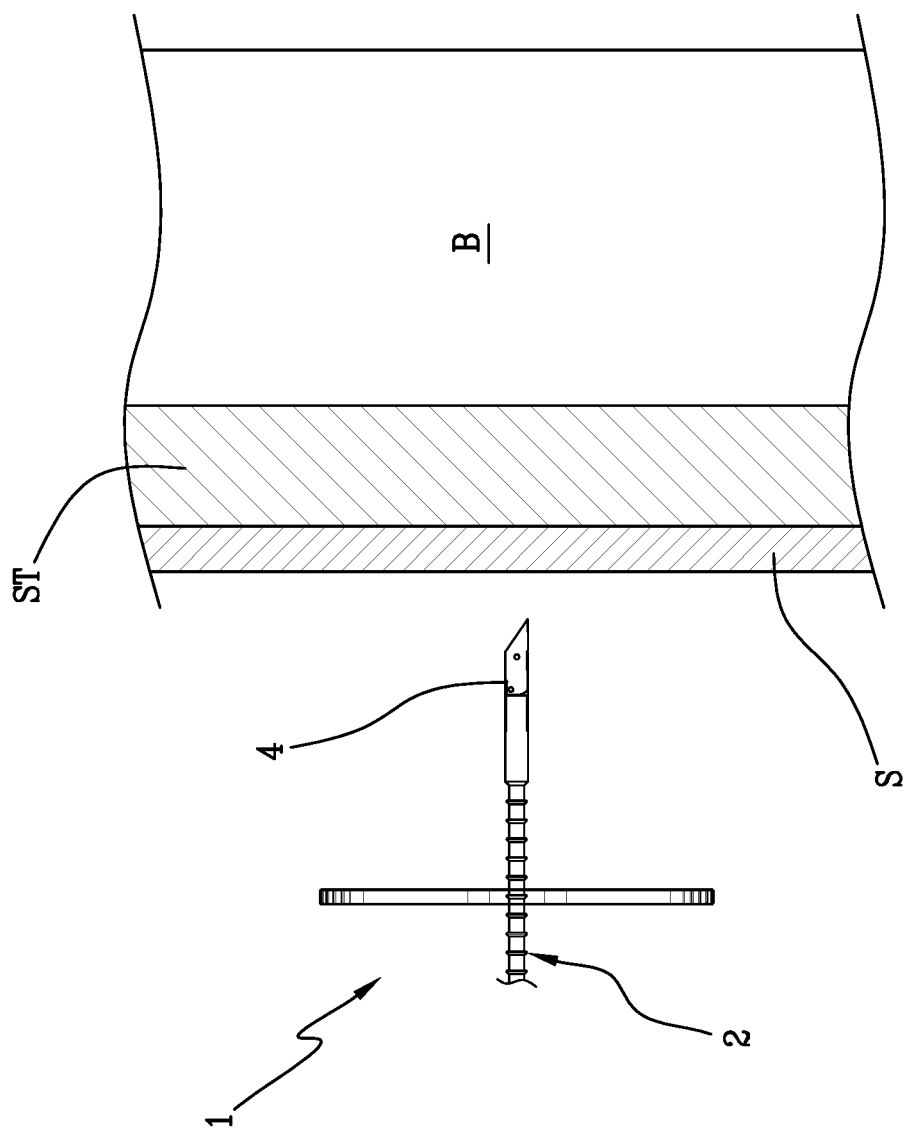

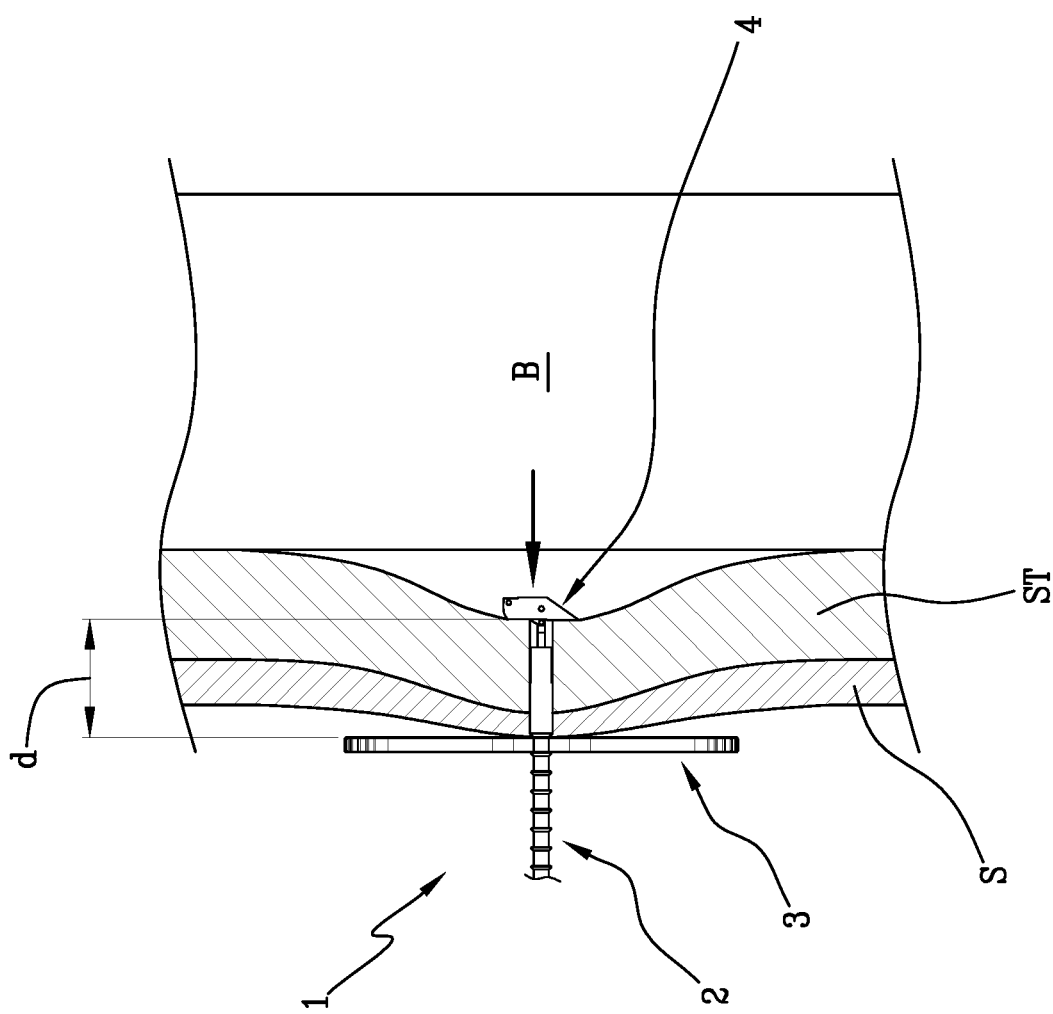

ed, Leroy retractors provide the possibility of having numerous configurations of the second free end, such as, for example, T-shaped ends, H-shaped ends, or the like.

DEVICE FOR THE RETRACTION OF SOFT TISSUE IN A PATIENT UNDERGOING ARTHROSCOPIC SURGERY

The present invention relates to a device for the retraction of soft tissue in a patient undergoing arthroscopic surgery.

Therefore, the present invention finds particular application in the surgical field, preferably the orthopaedic field, in tissue fixation equipment and in the preparation of the area to be operated.

In the context of surgical interventions intended to restore the normal articular mobility of an articulation of the human body, it is well known to arrange the operative site for the subsequent operations of restoration of the articular functionality. Because of the human anatomy, the preparation of the operative site requires the displacement of the soft tissue from its natural position adjacent to the patient's bone structure. This operation takes place by making an incision in the skin of the patient, creating therein an access for the entry of a special instrument, known as a retractor.

Currently, in order to increase the visibility, retraction instruments are used which, by means of special curved blades, cling to the edges of the wound from which the surgical tools are inserted, moving them away from each other.

These blades usually have a geometry such as to move not only the skin of the patient, but also the layers of soft tissue immediately adjacent thereto, so as to "open" the view to the surgeon.

Langenbeck and Volkmann retractors are cited merely as examples of retractors known in the state of the art.

Langenbeck retractor, for example, has a second end positioned at right angles to the elongated central structure, while Volkmann retractor has a second end at an angle of about 180 degrees with respect to the elongated central structure and connected thereto by means of a curved portion.

The use of such instruments derives directly from their function. After making an incision for access to the operative site, the retractor is inserted, the curved portion intercepting the soft tissue, thus moving it away from the proximity of the bone structure.

As will be easily recognized, said retractors are not easy to use in minimally invasive surgery, since their constructional features require a space for access to the operative site that is oversized compared to the minimally invasive surgery techniques.

Therefore, when the surgeon operates in minimally invasive situations, it is necessary to use retractors having variable geometry, so as to facilitate their insertion in the operative site. In fact, in operations of this type, the size of the access to the operative site is minimized as much as possible so as to inflict a small wound on the patient. This type of approach, however, does not allow the surgeon to have a good room for manoeuvre for operating by means of surgical instruments designed for a classic approach, for example an open surgery.

An example of a known retractor for minimally invasive surgery is the instrument known as the Leroy retractor. This device comprises an axially elongated structure with two free ends: a first one with a handle and a second with a variable geometry. In non-use conditions, the second end is axially aligned with the elongated structure. Once the instrument is inserted in the operative site, the surgeon, by means of a suitable command, can bend the second end up to an angle of 90 degrees with respect to the elongated structure, so as to intercept the soft tissue. At this point, by traction, the surgeon can remove the soft tissue from the operative site.

Leroy retractor is specially designed for laparoscopic operations. In this type of minimally invasive surgery, especially in colorectal laparoscopic surgery, a difficult anatomy (especially in obese male patients) makes it essential to use retractors to be able to clearly distinguish the different structures and make the intervention, for example the dissection, possible. Because of the particular nature of the type of surgery for which they are designed, Leroy retractors provide the possibility of having numerous configurations of the second free end, such as, for example, T-shaped ends, H-shaped ends, or the like.

However, during arthroscopy operations, the surgeon's needs are not simply to remove the soft tissue, as in the case of laparoscopy, but most closely match the needs of an open surgery, despite the fact that they are minimally invasive operations. In fact, during arthroscopic surgery, the surgeon needs to remove the soft tissue from the patient's bone structure in order to be able to access it and operate therein. As mentioned, however, the spaces are very narrow and the operative site cannot be accessed with typical instruments for open surgery.

It is also crucial for the surgeon not only to be able to remove the soft tissue from the bone structure, but also to reduce its dimensions in the whereabouts of the operative site, in order to facilitate the operation.

From the above, it therefore appears that the aforesaid objects cannot be achieved by means of equipment known in the state of the art, since, even though with arthroscopy access to the operative site with known instruments is hypothetically possible, it would not be possible to effectively remove the soft tissue from the bone structure.

Therefore, it is an object of the present invention to provide a device for the retraction of soft tissue in a patient undergoing arthroscopic surgery, which overcomes the above-mentioned drawbacks of the prior art.

In particular, it is an object of the present invention to provide a device for the retraction of soft tissue in a patient undergoing arthroscopic surgery, which is able to create the required operative space without compromising the integrity of the patient's soft tissue.

A further object of the present invention is to provide a device for the retraction of soft tissue, which is easily adjustable and easy to use.

Said objects are achieved by means of a device for the retraction of soft tissue having the features of one or more of the ensuing claims.

In particular, the retraction device comprises a pulling element extending in its own main direction between a first end and a second end.

Preferably, the second end is fitted with a hooking body configured to pass through the soft tissue of a patient and engage (or intercept) said soft tissue following the traction of the pulling element towards the first end.

According to one aspect of the present invention, the device further comprises a presser body adapted to press on the skin of said patient and connectable to the pulling element in at least one operating position placed at a fixed distance from the second end.

Preferably, the fixed distance is such as to define a housing for the layers of the patient's soft tissue engaged by the hooking body, so as to compress it and consequently create the operative space between the bone and the tissue.

Therefore, the presser body 3 is connected to the pulling element 2 so as to define therewith a clamp in which the soft tissues ST are compressed. Advantageously, thanks to this device, no traction is exerted any more on the soft tissue moving away from the bone, but said tissue is compressed so as to reduce the thickness thereof, which brings about the detachment of tendons and muscle bundles atraumatically.

In particular, thanks to this device, it is possible to implement a retraction method innovative per se, according to which the retraction of the soft tissue comprises limiting the distal displacement of the skin from the bone portion by means of a presser body abutted against the skin of the patient and compressing the layers of soft tissue towards said presser body (i.e. away from the bone but without traction) so as to create an operative space.

Advantageously, thanks to this innovative principle, the efficiency of the operation can be combined with a reduced invasiveness of the same, which helps to reduce the patients' recovery time.

It should preferably be noted that the presser body is slidingly joined to the pulling element to move from a rest position, distal to the second end, to said operating position, proximal to the second end.

More preferably, blocking means are provided which are configured to prevent the presser body from moving away from the second end when in said operating position, thus allowing the correct compression of the tissues interposed between the presser body and the hooking body.

In the preferred embodiment, the unidirectional sliding and blocking are obtained by means of a ratchet coupling of the presser body on the pulling element.

Preferably, moreover, the presser body has a pincer or clothes peg shape so as to be able to couple to and uncouple from the pulling element following a (manual) command given by the operator.

These and other features and the inherent advantages will become more apparent from the following illustrative, therefore non-limiting, description of a preferred, thus not exclusive, embodiment of a device for the retraction of soft tissue in a patient undergoing arthroscopic surgery as shown in the accompanying drawings, wherein:

FIGS. 3 and 4 show a plan view and the corresponding longitudinal section of the device in FIG. 1;

FIGS. 5a-5c show successive steps of a method of retraction of soft tissue in a patient undergoing arthroscopic surgery implemented by means of the device of FIG. 1.

Figure 1:
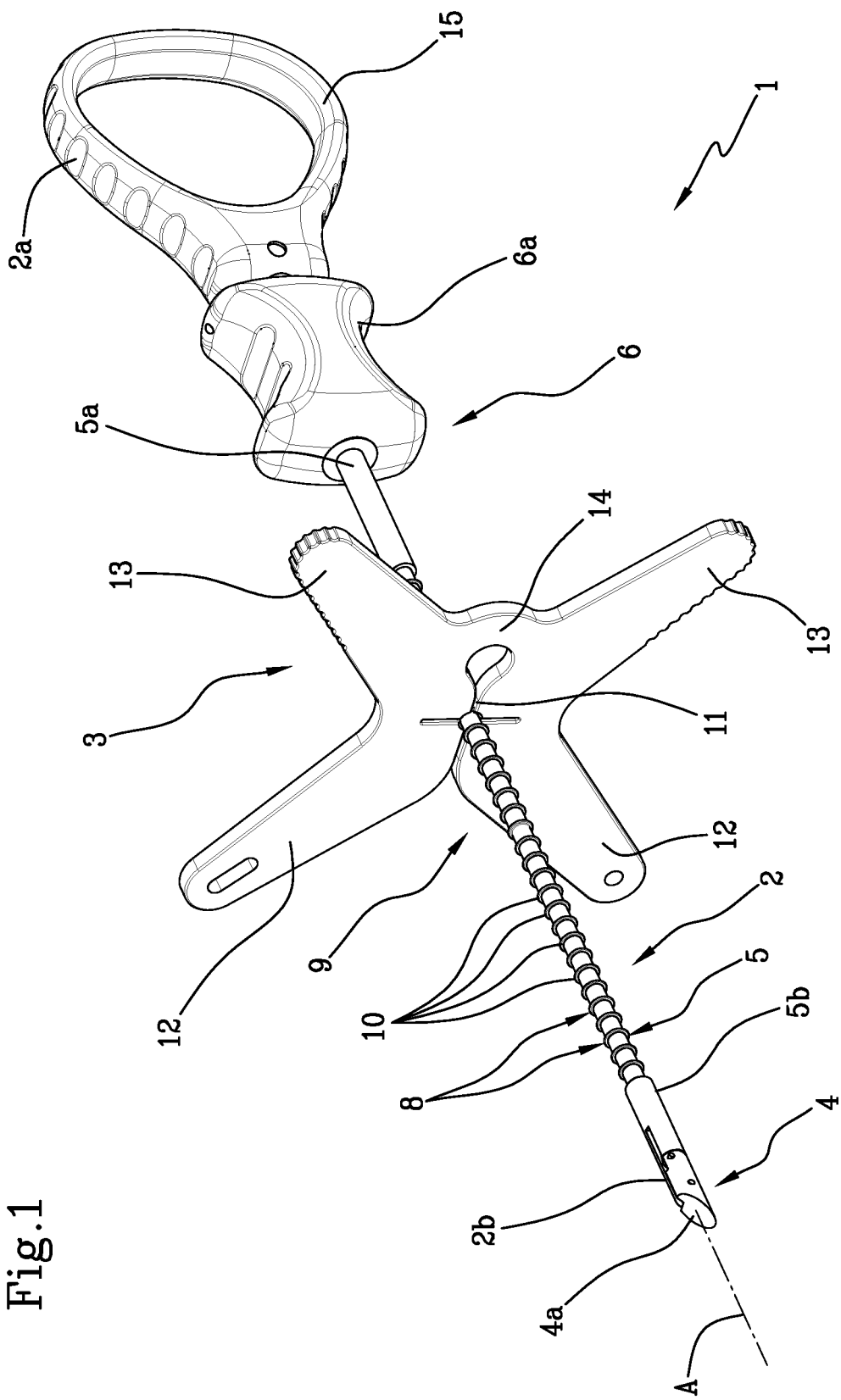
FIGS. 1 and 2 show two perspective, front and rear views of a device for the retraction of soft tissue in a patient undergoing arthroscopic surgery according to the present invention.
Figure 2:
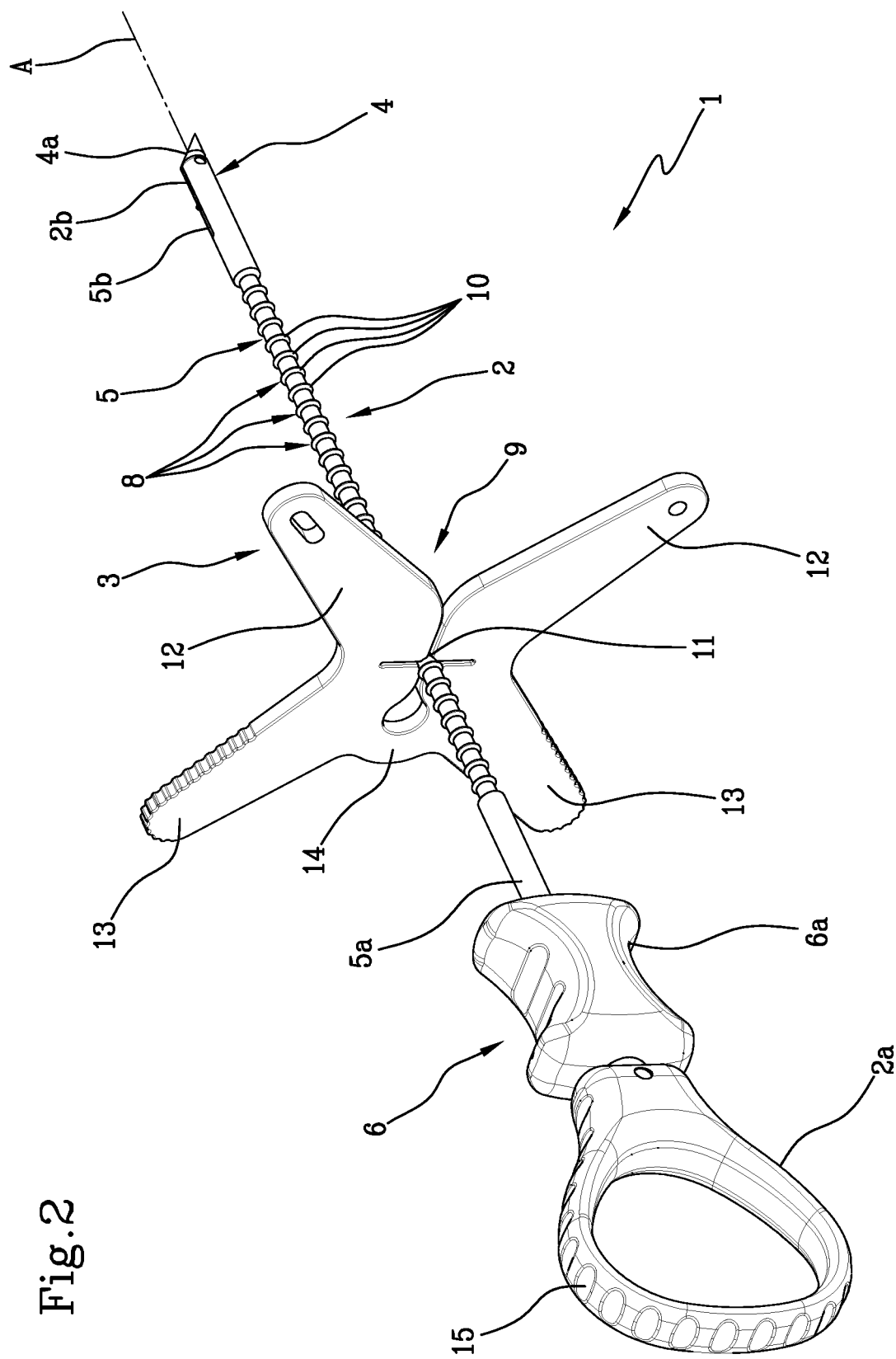
Figure 5B:
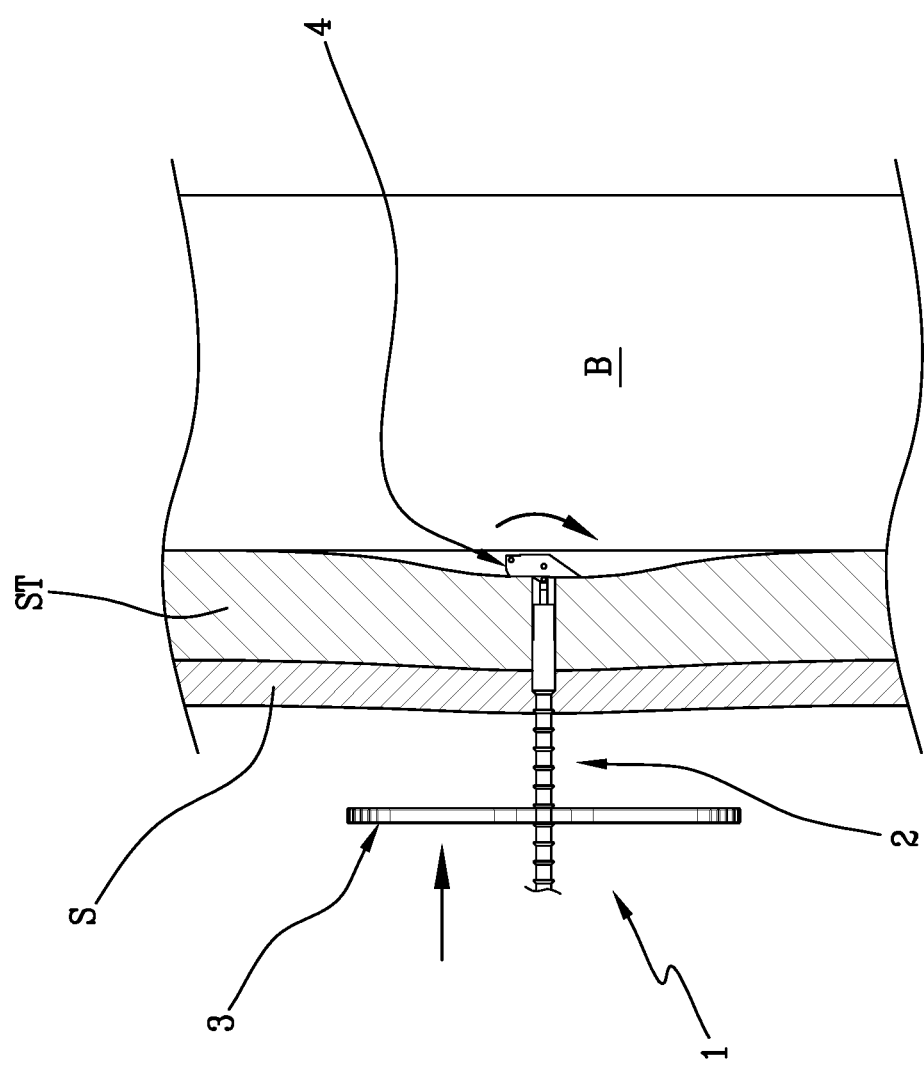

With reference to the accompanying figures, the numeral 1 indicates a device for the retraction of soft tissue in a patient undergoing arthroscopic surgery according to the present invention.

It should be noted that in the present text "soft tissues" is intended to mean all such tissues with a density different from that of the bone and therefore distinguishable and separable from the bone.

By way of example, soft tissues can be one or more of the following:
 muscles,
 tendons,
 fat,
 synovia,
 vessels,
 nerves,
 connective tissue proper or interstitial tissue (supporting the parenchyma),
 supportive connective tissue, such as for example cartilages.

Therefore, the device 1 finds application in the creation of a gap or a distance between the bone "B" and the soft tissue "ST" during a surgical, preferably orthopaedic operation, more preferably an arthroscopy.

The device 1 preferably comprises a pulling element 2 and a presser body 3.

The pulling element 2 extends along its own main direction "A" between a first end 2a and a second end 2b.

Preferably, the first end 2a is free and can be gripped or manoeuvred by an operator, i.e. the surgeon.

In the illustrated embodiment, the first end 2a is provided with a handle 15, in order to assist the surgeon in manoeuvring the device 1.

Also preferably, the second end 2b, instead, is fitted with a hooking body 4 configured to pass through the patient's soft tissue "ST" and engage the same following the traction of the pulling element 2 towards the first end 2a.

In other words, the hooking body 4 is shaped so that, once inserted through the soft tissues "ST" by moving it proximally (i.e. towards the bone), it can intercept the soft tissues "ST", pushing them distally (i.e. away from the bone) when the pulling element is moved in the direction of the first end 2a.

In the preferred embodiment, the pulling element 2 comprises a stem 5 extending along the main direction "A" between its own first 5a and its own second 5b end portion.

The end portions 5a, 5b of the stem substantially correspond to the ends 2a, 2b of the pulling element 2.

Therefore, the hooking body 4 is joined to the second end portion 5b of the stem 5.

Preferably, the hooking body 4 is rotatably joined to the stem 5, at the second end portion 5b (i.e. the second end of the pulling element 2).

In particular, the hooking body 4 can rotate so as to move between a first position, in which it is substantially aligned with the stem 5, and a second position, in which it is substantially transverse to the stem 5 (i.e. to the main direction "A").

In the preferred embodiment, the hooking body 4 is pivoted (preferably at a central portion thereof) to the second end portion 5b of the stem 5.

Advantageously, in this way, the pulling element 2 can easily penetrate the skin "S", passing through the soft tissues "ST", with the hooking body 4 in the first position.

In this regard, the hooking body 4 preferably comprises a tapered end portion 4a so that, when it is in said first position, it defines with the stem 5 an instrument able to penetrate the soft tissue "ST" of the patient.

By moving the hooking body 4 into the second position, instead, a non-extractable anchor is obtained which, with the body penetrated inside the soft tissues "ST", intercepts them; as a result of a movement or traction of the pulling element 2 in the direction of the first end 2a, therefore, the hooking body 4 in the second position retracts the soft tissues "ST" away from the bone, thus creating space in the operative site.

In order to allow the hooking body 4 to be moved easily, the pulling element 2 comprises a manoeuvring group 6 operable by an operator and joined to the hooking body 4.

This manoeuvring group 6 is configured to move the hooking body 4 between the first and the second position.

More precisely, the manoeuvring group 6 preferably comprises a control body 6a, manoeuvrable by the operator, and a transmission member 6b operatively interposed between the control body 6a and the hooking body 4.

Advantageously, the surgeon by acting manually on the control body 6a can thus move the hooking body 4 between the first and the second position.

In the preferred embodiment, the transmission member 6b comprises a rod (or a cable) 7 slidingly inserted in the stem 5 and connected to the hooking body 4.

In particular, this rod (or cable) 7 is connected to the hooking body 4 so that a translation thereof corresponds to a rotation of the hooking body 4. In this regard, preferably, the control body 6a is a ring nut or sleeve movable by the surgeon towards or away from the first end 2a of the pulling element 2 in order to move the transmission member 6b.

If the control body 6a is a ring nut, its translation is obtained by means of a threaded coupling to the stem 5 and the rotation thereof.

If the control body 6a is a sleeve (shown), its translation occurs directly, by means of a pushing or pulling action by the surgeon.

In order to allow the correct retraction of the soft tissue "ST", as said, the device 1 also comprises a presser body 3 joined to the pulling element 2. According to one aspect of the present invention, the presser body 3 is adapted to press on the skin "S" of the patient and connectable to the pulling element 2 in at least one operating position placed at a fixed distance "d" from the second end 2a.

This fixed distance "d" is such as to define a housing for the layers of soft tissue "ST" of the patient engaged by the hooking body 4.

In other words, the presser body 4 is connected to the pulling element 2 so as to define therewith a clamp in which the soft tissues "ST" are compressed, in order to detach them from the bone.

Preferably, the operating position (and hence the distance d) is variable and adjustable according to the thickness of the patient's soft tissues "ST", which may be of different levels proportionally to the thickness of the tendons, muscles and fatty layer.

In this regard, the presser body 3 is preferably slidingly joined to the pulling element 2 to move from a rest position, distal to the second end 2a, to said operating position, proximal to the second end 2b.

In order to maintain the position, and hence the pressure that allows the tissues to be compressed, the device 1 comprises blocking means 8 operatively interposed between said presser body 3 and the pulling element 2.

The blocking means 8 are configured to prevent the presser body 3 from moving away from the second end 2b when said presser body 3 is in said operating position.

Therefore, the presser body 3 is preferably slidingly joined to the pulling element 2 unidirectionally, i.e. free to slide from the first end 2a to the second end 2b.

The blocking means 8 prevent sliding in the opposite direction.

Preferentially, the presser body 3 is slidingly joined to the pulling element 2 by means of a tightener group 9.

This tightener group 9 is configured to allow an increase in the contact pressure between the presser body 3 and the skin "S" of the patient, at least when the presser body 3 is in the operating position.

In the preferred embodiment, the tightener group 9 comprises a ratchet coupling.

More precisely, the ratchet coupling comprises a plurality of abutment shoulders 10 arranged in succession along the pulling element 2 (defining said blocking means 8) and at least one abutment tooth 11 joined to the presser body 3.

The abutment tooth 11 is shaped to slide along the pulling element 2 (and along the abutment shoulders 10) from the first 2a to the second 2b end and halt against the abutment shoulders 10 if moved from the second 2b to the first 2a end.

In the preferred embodiment, the pulling element 2 (in particular the stem 5) has a sawtooth side profile.

The inclined surface of each tooth extends gradually away from the stem 5 towards the second end 5b and allows the tooth 11 of the presser body 3 to slide in this direction.

The steep surface of each tooth extends substantially perpendicular from the top to the stem 5, defining an abutment shoulder 10 and preventing the tooth 11 of the presser body 3 from sliding away from the second end 5b.

Preferably, moreover, the presser body 3 is selectively switchable between an engaged condition, in which it is slidingly connected to the pulling element 2, and a disengaged condition, in which it is releasable (or released) from the pulling element 2.

Advantageously, in this way, once the operation is terminated or in case of necessary and further adjustments, it is possible to detach the presser body 3 from the pulling element 2, for example by moving the presser body away from the second end 2b (which would not be possible in the engaged condition).

In the preferred embodiment, in order to allow such switching, said presser body 3 has a pincer or clothes peg shape.

More precisely, the presser body 3 comprises two jaws 12 reciprocally moving towards and away from each other between a juxtaposed position, defining said engaged condition, and a distant position, defining said disengaged condition.

In the juxtaposed position, between the two jaws 12 there is a gap for the passage of the pulling element 2; said gap is peripherally bounded by an edge defining the abutment tooth 11.

It should be noted that, preferably, the presser body 3 has a normally closed configuration in which the jaws 12 are in the juxtaposed position (i.e. in the engaged condition).

Preferably, the jaws 12 are therefore maintained in the juxtaposed position by elastic means.

In order to move the presser body 3 between the two positions, it is provided with a pair of movement arms 13, each joined to a respective jaw 12, reciprocally moving towards and away from each other between a proximal position, in which they keep the jaws 12 spaced apart in the distant position corresponding to the normally closed configuration of the presser body 3.

In other words, between the arms 13 and the jaws 12 there is a fulcrum 14 which allows the movement to be transferred from one to the other (defining a first class lever).

The fulcrum 14 therefore defines a deformable elastic means which allows the jaws 12 to be opened/closed, keeping them in the juxtaposed position in the absence of external stresses.

Thanks to the device 1 (but not exclusively), it is therefore possible to implement an innovative method of retraction of soft tissue in a patient undergoing arthroscopic surgery.

This method comprises incising and penetrating one or more layers of soft tissue "ST" proximal to a bone portion "B" to be operated and retracting said layers of soft tissue "ST" away from the bone portion "B" in order to create a space in the operative site.

According to this innovative method, the retraction of the soft tissues "ST" is obtained by limiting the distal displacement of the skin "S" from the bone portion "B" by means of a presser body 3 abutted against the skin "S" and compressing said one or more layers of soft tissue "ST" towards said presser body 3 so as to create a space in the operative site.

Advantageously, the tendons and all the tissues are preserved as no traction is exerted thereon (or only to a very small extent) when they move away from the bone.

On the contrary, it is the tissue layers closest to the bone that are "pushed" towards the presser body 3, which however prevents the same displacement of the tissue layers furthest from the bone (epidermis), generating the compression thereof.

Preferably, the compression is in fact achieved by tightening the presser body 3, abutted externally against the skin "S", against a pulling element 2 fitted with at least one hooking body 4 inserted through said one or more layers of soft tissue "ST".

Preferably, but not exclusively, the presser body 3 and the pulling element 2 are of the type described previously with regard to the device 1 object of the present invention.

However, this method could possibly also be implemented with other devices suitable to allow compression of the soft tissue "ST".

The invention achieves the intended objects and attains important advantages.

In fact, as already pointed out several times, the presence of a presser body and a pulling element defining a clamp allows the soft tissue to be compressed without subjecting it to traction, which clearly eliminates the risk of damaging or inflaming the same tissues.

Moreover, the use of a single pulling element switchable between two configurations, i.e. the penetrating and the hooking configuration, allows the retraction procedure to be simplified and sped up.

In this respect, the presence of a ratchet coupling or a tightener group between the presser body and the pulling element is particularly advantageous since it allows the "operating position" to be adapted to the individual patient without the need for dedicated devices.

The invention claimed is:

1. A device for the retraction of soft tissue in a patient undergoing arthroscopic surgery, comprising:
    a pulling element extending in its own main direction between a first end and a second end, said second end being fitted with a hooking body configured to pass through the soft tissue of a patient and engage in said soft tissue following the traction of the pulling element towards the first end; and
    a presser body suitable to press on the skin of said patient and connectable to the pulling element in at least one operating position placed at a fixed distance from the second end, said fixed distance being such as to define a housing for the layers of soft tissue of the patient engaged by the hooking body,
    wherein the pulling element comprises a stem extending in the main direction between the first end and the second end, the hooking body being rotatably joined to the stem, at the second end, to move between a first position, in which the hooking body is aligned with the stem, and a second position, in which the hooking body is transverse to the stem,
    wherein the pulling element comprises a maneuvering group operable by an operator and joined to the hooking body to move the pulling element between the first position and the second position, the maneuvering group comprising:
        a control body maneuverable by the operator; and
        a transmission member operatively interposed between the control body and the hooking body and comprising a rod or cable slidingly inserted in the stem and connected to the hooking body so that a translation of the rod or cable corresponds to a rotation of the hooking body.

2. The device according to claim 1, wherein said presser body is connected to the pulling element so as to define therewith a clamp configured to compress the soft tissues.

3. The device according to claim 1, wherein said presser body is slidingly joined to the pulling element to move from a rest position, distal to the second end, to said operating position, proximal to the second end.

4. The device according to claim 1, further comprising blocking agents operatively placed between said presser body and said pulling element and configured to prevent the presser body from moving away from the second end when in said operating position.

5. The device according to claim 4, wherein said presser body is slidingly joined to the pulling element via a tightener group configured to increase the contact pressure between the presser body and the skin of the patient.

6. The device according to claim 5, wherein said tightener group comprises a ratchet coupling.

7. The device according to claim 6, wherein said ratchet coupling comprises:
    a plurality of abutment shoulders arranged in succession along the pulling element; and
    at least one abutment tooth joined to the presser body and shaped to slide along the pulling element from the first to the second end and to halt against said abutment shoulders if moved from the second to the first end.

8. The device according to claim 1, wherein said presser body is selectively switchable between an engaged condition, in which the presser body is slidingly connected to the pulling element, and a disengaged condition, in which the presser body is releasable from the pulling element.

9. The device according to claim 8, wherein said presser body has a pincer or clothes peg shape.

10. The device according to claim 8, wherein said presser body comprises two jaws reciprocally moving towards and away from each other between a juxtaposed position, defining said engaged condition, and a distant position, defining said disengaged condition.

11. The device according to claim 10, wherein said presser body has a normally closed configuration in which the jaws are in said juxtaposed position; said presser body comprising a pair of movement arms, each joined to a respective jaw, reciprocally moving towards and away from each other between a proximal position, in which the movement arms keep the jaws spaced apart in the distant position corresponding to the normally closed configuration of the presser body.

12. The device according to claim 1, wherein the hooking body comprises a tapered end portion so that, when the hooking body is in said first position, the hooking body defines with the stem an instrument able to penetrate the soft tissue of the patient.

* * * * *